United States Patent [19]

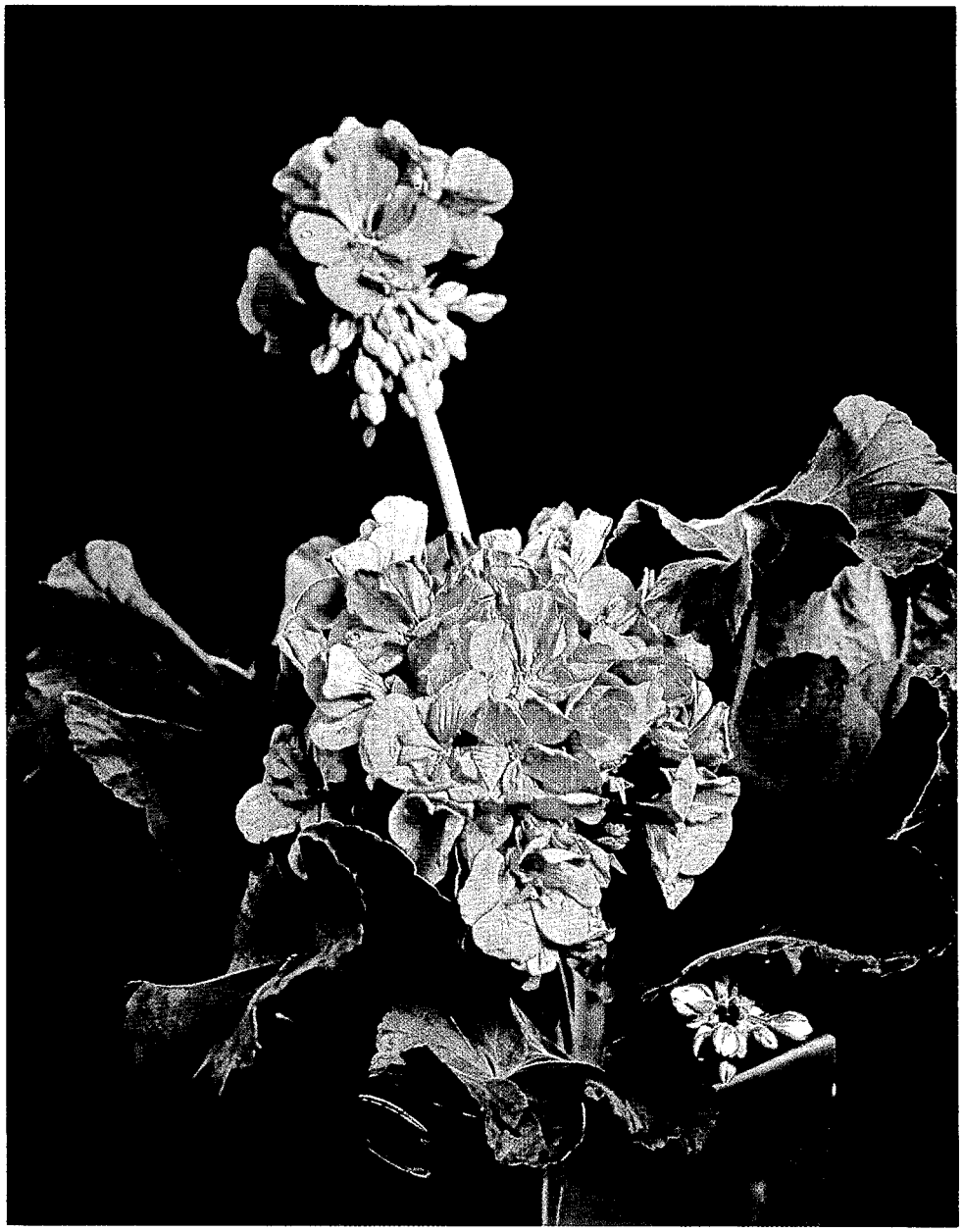

Buck

[11] Plant 4,039

[45] Apr. 12, 1977

[54] GERANIUM PLANT NAMED PEARLIE MAE RED

[75] Inventor: Griffith J. Buck, Ames, Iowa

[73] Assignee: Iowa State University Research Foundation, Inc., Ames, Iowa

[21] Appl. No.: 680,151

[22] Filed: May 3, 1976

[51] Int. Cl.[2] ..... A01H 5/00

[52] U.S. Cl. ..... Plt./68

[58] Field of Search ..... Plt./68

*Primary Examiner*—Robert E. Bagwill

*Attorney, Agent, or Firm*—Rummler and Snow

[57] ABSTRACT

A new geranium cultivar distinguished by its ability to grow vigorously and flower profusely under high humidity and temperature conditions, a shorter time requirement to initiate inflorescence, and by the very large size of the florets and floret clusters which comprise the blooms.

1 Drawing Figure

BACKGROUND OF THE NEW PLANT

My new geranium cultivar originated as a seedling resulting from my crossing a cultivar of the unpatented varieties "Cardinal" × "Galaxie" with "Galaxie" at Ames, Iowa, during a hybridization program carried on by me at Ames, Iowa, since 1956. The new plant was discovered by me in October 1970 among progeny of the principal cross and was selected for propagation and trail because of its vigorous growth habit under high temperature and humidity conditions, the extraordinarily large size of its inflorescence and its profuse production of blooms. Since its discovery propagation of the new plant by cuttings has been carried on under my direction at Iowa State University, at Ames, Iowa, through numerous generations which have demonstrated that the distinctive characteristics of this new plant hold true from generation to generation and are firmly fixed. Propagation of this new geranium cultivar is now being done by cuttage at Iowa State University.

DESCRIPTION OF THE DRAWING

My new geranium cultivar is illustrated by the accompanying photographic drawing which shows a fully developed flower, buds and foliage in full color, the colors shown being as nearly true as it is reasonably possible to reproduce by conventional photographic procedures.

DESCRIPTION OF THE NEW PLANT

The following is a detailed description of my new geranium cultivar with color designations according to the Robert F. Wilson Horticultural Colour Chart published by the Royal Horticultural Society of London, England, in collaboration with the British Colour Council, the data being obtained by observations of the new plant made at Iowa State University, at Ames, Iowa.

THE PLANT

Origin: Seedling.

Parentage:

*Seed parent.*—An unnamed and unpatented seedling of "Cardinal" × "Galaxie" (both unpatented).

*Pollen parent.*—"Galaxie".

Classification:

*Botanic.*—Pelargonium hortorum, Bailey.

*Commercial.*—Garden geranium.

Form: Bush.

Height: 35 to 45 cm. × 35 to 45 cm. outdoors; 30 × 30 cm. as a 4 inch pot plant.

Growth: Vigorous, upright and branching.

Strength: Sturdy; does not break apart readily in wind and rain.

Foliage: Quantity — abundant.

*Leaves.*—Size: 9 to 13 cm. × 10 to 13 cm. Shape: Round-cordate with several rounded lobes with serrate margins. Texture: Leathery and slightly pubescent on both surfaces which feel "hard" to the touch. Color: Upper side — somewhat darker than Spinach Green 0960 (HCC) with an indistinct center zone of Spinach Green 0960/1 (HCC). Under side — Spinach Green 0960/2 Ribs and Veins: Not prominent on upper surface; conspicuous on lower surface.

*Petioles.*—8 to 11 cm. long.

*Stipules.*—7 to 8 mm. wide × 1.2 to 1.4 cm. long. Shape: Ovoid-pointed. Color: Spinach Green 0960/1 (HCC) paling to Scheeles Green 860/3 (HCC).

*Stem.*—Internodes, short — averaging 1.5 to 3.0 cm. in length. Aspect: Slightly hairy. Color: Scheeles Green 860/2 (HCC).

THE BUD

Size: Large; 1.3 to 1.5 cm. long × 6 to 8 mm. in diameter.

Form: Pointed ovoid.

Opening: Bud opens slowly.

Color:

*When sepals first divide.*—Dutch Vermilion 717 (HCC).

*When petals begin to unfurl.*—Dutch Vermilion 717 (HCC).

Sepals: 5 separate sepals which stand up at first and then curl back as floret fully opens.

*Color.*—Inside — Scheeles Green 860/3 (HCC). Outside — Scheeles Green 860/3 tinted with Dutch Vermilion 717 (HCC).

*Aspect.*—Hairy on outer surface.

THE FLOWER

Blooming Habit: Continuous and profusely through the growing season; under glass and with adequate photoperiod, this plant will flower all year.

Size: Very large — Diameter 10 to 15 cm., Depth 5 to 8 cm.

Borne: Singly; the inflorescence is umbel-form.

Shape: A compact, approximately globular umbel.

Florets:

*Form.*—Flat to slightly cup-shaped.

*Size.*—4.5 to 4.7 cm. in diameter.

*Petals.*—Eight to 11 in number, including petaloids. Arrangement: Imbricate. Shape: Obovate. Color: Outer petals — Dutch Vermilion 717 (HCC) with a small white tip at base. Inside petals — Dutch Vermilion 717. Reverse side — Dutch Vermilion 717/2 with white on basal portion and along veins. Texture: Firm. Appearance: Satiny.

*Petaloids.*—None to three in number. Size: 1.5 to 1.7 cm. long, 4 to 6 mm. wide. Shape: Semi-tubular, curled or flat. Color: Dutch Vermilion 717 (HCC)

*Pedicel.*—Length — 1.5 to 2.2 cm. Aspect: Strong and slightly hairy.

*Peduncle.*—Length — 10 to 23 cm. Growth: Sturdy and upright. Color: Scheeles Green 860/2 (HCC).

Persistence of Bloom: Petals hang on and dry.

Discoloration after Full Bloom: Petals darken with age.

Disease Resistance: Plant is tolerant of Botrytis cinerea.

Lasting Quality: About 7 days.

REPRODUCTIVE ORGANS

Stamens:

*Anthers.*—Seven to 10 in number. Length: 3 mm.

Arrangement: Cylindrical.

*Filaments.*—Length — 5 to 7 mm. Color: White.

*Pollen.*—Color — Brownish yellow.

Pistils: Number — 1, 3 to 4 mm. long.

*Stigma.*—Color — red.

Ovaries: 5-celled

Fruit: Partially fertile.

*Shape.*—Ovoid with a long "beak".

*Color at Maturity.*—Brownish black.

The floral color of this new geranium cultivar is similar to that of the variety "Orange Glow" (unpatented) but has greater intensity and brilliance. The plant habit is similar to that of the pollen parent "Galaxie" in that it is equally tolerant of high temperatures and humidity and has the ability to grow vigorously and flower profusely under those climatic conditions. Also, this new plant has shown a high tolerance, under field conditions, to Botrytis cinerea Pers. This cultivar differs from its parents by having a more profuse flowering habit due to a shorter time period for the initiation of inflorescences which are produced on a 2–4 node cycle.

I claim:

1. A new and distinct geranium cultivar substantially as herein shown and described, characterized by its profuse production of very large umbel-form inflorescence, its ability to flower throughout the year under glass, its generally shorter time requirement for initiation of inflorescence, and its ability to grow vigorously and flower profusely under high humidity and temperature conditions.

* * * * *

UNITED STATES PATENT OFFICE

CERTIFICATE OF CORRECTION

Patent No. PP 4039 Dated April 12, 1977

Inventor(s) Griffith J. Buck

It is certified that error appears in the above-identified patent and that said Letters Patent are hereby corrected as shown below:

The drawing figure, as shown, should be deleted and substituted with the attached drawing figure therefor.

THIS CERTIFICATE APPLYS TO THE GRANT ONLY

Signed and Sealed this

*Twenty-second* Day of *November 1977*

[SEAL]

*Attest:*

RUTH C. MASON
*Attesting Officer*

LUTRELLE F. PARKER
*Acting Commissioner of Patents and Trademarks*